(12) United States Patent
Herritz et al.

(10) Patent No.: US 11,499,809 B2
(45) Date of Patent: Nov. 15, 2022

(54) TAPE MEASURE WITH PROTECTIVE BUMPER

(71) Applicant: Milwaukee Electric Tool Corporation, Brookfield, WI (US)

(72) Inventors: Devin W. Herritz, Sussex, WI (US); Patrick W. McCarthy, Milwaukee, WI (US)

(73) Assignee: Milwaukee Electric Tool Corporation, Brookfield, WI (US)

(*) Notice: Subject to any disclaimer, the term of this patent is extended or adjusted under 35 U.S.C. 154(b) by 57 days.

(21) Appl. No.: 17/110,031

(22) Filed: Dec. 2, 2020

(65) Prior Publication Data

US 2021/0088318 A1 Mar. 25, 2021

Related U.S. Application Data

(63) Continuation of application No. PCT/US2020/035707, filed on Jun. 2, 2020.

(60) Provisional application No. 62/856,483, filed on Jun. 3, 2019.

(51) Int. Cl.
*G01B 3/1046* (2020.01)
*G01B 3/1005* (2020.01)
*G01B 3/1056* (2020.01)

(52) U.S. Cl.
CPC ......... *G01B 3/1046* (2020.01); *G01B 3/1005* (2013.01); *G01B 3/1056* (2013.01); *G01B 2003/103* (2013.01)

(58) Field of Classification Search
CPC .. G01B 3/1046; G01B 3/1005; G01B 3/1056; G01B 2003/103; G01B 3/1041
See application file for complete search history.

(56) References Cited

U.S. PATENT DOCUMENTS

| 3,192,630 | A | | 7/1965 | Dineson |
| 4,363,171 | A | | 12/1982 | Scandella |
| 4,479,617 | A | * | 10/1984 | Edwards .............. G01B 3/1005 242/380 |
| 4,908,954 | A | | 5/1990 | Johnson |
| 5,189,801 | A | | 3/1993 | Nicely |
| D342,459 | S | | 12/1993 | Shen |
| 5,829,152 | A | | 11/1998 | Potter et al. |
| 6,115,931 | A | | 9/2000 | Arcand |
| 6,598,310 | B1 | | 7/2003 | Odachowski |
| 6,663,153 | B2 | | 12/2003 | Brunson |

(Continued)

FOREIGN PATENT DOCUMENTS

| CN | 2476791 Y | 2/2002 |
| CN | 1696600 A | 11/2005 |

(Continued)

OTHER PUBLICATIONS

International Search Report and Written Opinion for PCT Application No. PCT/US2020/035707 dated Sep. 11, 2020 (11 pages).

*Primary Examiner* — Yaritza Guadalupe-McCall
(74) *Attorney, Agent, or Firm* — Reinhart Boerner Van Deuren s.c.

(57) ABSTRACT

A tape measure including an elongate tape blade is shown. The tape measure includes a protective bumper that extends below the tape opening. The bumper is shaped to allow the tape hook to pivot during drop or impact to reduce the impact force experienced by the tape hook.

20 Claims, 9 Drawing Sheets

(56) References Cited

U.S. PATENT DOCUMENTS

| | | | |
|---|---|---|---|
| 6,678,967 B1 | 1/2004 | Juenemann | |
| 7,003,895 B2 * | 2/2006 | Harris | G01B 3/1005 242/378 |
| 7,124,515 B2 | 10/2006 | Juenemann | |
| 7,174,656 B1 | 2/2007 | Smith | |
| 7,266,905 B1 | 9/2007 | Lee | |
| 7,458,537 B2 * | 12/2008 | Critelli | G01B 3/1005 242/376 |
| 7,475,492 B1 | 1/2009 | Huang | |
| 7,669,347 B1 | 3/2010 | Huang | |
| 7,805,855 B2 | 10/2010 | Seo | |
| 8,806,770 B2 * | 8/2014 | Steele | G01B 3/1041 33/761 |
| 8,863,399 B2 * | 10/2014 | Steele | G01B 3/1003 33/679.1 |
| 8,898,922 B2 | 12/2014 | Bridges et al. | |
| 9,161,578 B1 | 10/2015 | Andreasen | |
| 9,322,628 B2 | 4/2016 | Burch | |
| 9,952,027 B2 | 4/2018 | Burch et al. | |
| 2003/0019116 A1 | 1/2003 | DeWall | |
| 2004/0060188 A1 | 4/2004 | Cubbedge | |
| 2004/0064961 A1 * | 4/2004 | Harris | G01B 3/1005 33/755 |
| 2004/0181959 A1 | 9/2004 | Juenemann | |
| 2006/0112582 A1 | 6/2006 | Scarborough | |
| 2007/0074418 A1 | 4/2007 | Critelli et al. | |
| 2008/0034604 A1 * | 2/2008 | Critelli | G01B 3/1005 33/767 |
| 2009/0249636 A1 | 10/2009 | Reda et al. | |
| 2009/0288307 A1 | 11/2009 | Zhou | |
| 2010/0175273 A1 | 7/2010 | Sea | |
| 2012/0073156 A1 | 3/2012 | DeLaRosa | |
| 2013/0025147 A1 * | 1/2013 | Steele | G01B 3/1041 33/769 |
| 2013/0047455 A1 | 2/2013 | Steele et al. | |
| 2013/0133215 A1 | 5/2013 | Bridges et al. | |
| 2013/0185949 A1 * | 7/2013 | Burch | G01B 3/1061 33/768 |
| 2014/0352165 A1 * | 12/2014 | Steele | G01B 3/1005 33/768 |
| 2015/0047216 A1 * | 2/2015 | Burch | G01B 3/1056 33/770 |
| 2016/0061573 A1 | 3/2016 | Kamani et al. | |
| 2017/0089682 A1 * | 3/2017 | Feuerstein | G01B 3/1041 |
| 2017/0292821 A1 | 10/2017 | DeLeo et al. | |
| 2019/0242686 A1 | 8/2019 | Reddy et al. | |
| 2021/0088318 A1 * | 3/2021 | Herritz | G01B 3/1041 |

FOREIGN PATENT DOCUMENTS

| | | |
|---|---|---|
| CN | 202660995 U | 1/2013 |
| JP | 2003-279303 | 10/2003 |
| JP | 2004257747 | 9/2004 |
| JP | 2007033251 | 2/2007 |
| KR | 200385910 | 6/2005 |
| KR | 100921157 | 10/2009 |
| KR | 1020150114205 | 10/2015 |

\* cited by examiner

TAPE MEASURE WITH PROTECTIVE BUMPER

CROSS-REFERENCE TO RELATED PATENT APPLICATIONS

The present application is a continuation of International Patent Application No. PCT/US2020/035707, filed Jun. 2, 2020, which claims the benefit of and priority to U.S. Provisional Application No. 62/856,483, filed on Jun. 3, 2019, which are incorporated herein by reference in their entireties.

BACKGROUND OF THE INVENTION

The present disclosure relates generally to the field of tape measures. The present disclosure relates specifically to a tape measure with a protective bumper located below the tape blade opening.

Tape measures are measurement tools used for a variety of measurement applications, including in the building and construction trades. Some tape measures include a graduated, marked blade wound on a reel and a retraction system for retracting the blade onto the reel. In some tape measure designs, the retraction system is driven by a coil or spiral spring that is tensioned, storing energy as the tape is extended, and that releases energy to spin the reel, winding the blade back onto the reel.

SUMMARY OF THE INVENTION

One embodiment of the disclosure relates to a tape measure with a bumper coupled to the housing. The bumper defines a shoulder and a recess portion. The shoulder extends outward away from a front face of the tape measure further than the recessed portion. The tape measure comprises an elongate tape blade that transits an opening in the housing. A hook assembly is coupled to an end of the tape blade. The hook assembly comprises an upper hook that extends above the tape blade and a lower hook that extends below the tape blade. In a specific embodiment, the upper blade comprises a pair of wings that extend above the tape blade and away from the primary axis of the elongate tape blade.

The upper hook extends above the blade defining an upper hook height, and the recess portion defines a recess width as the perpendicular distance measured between a front face of the tape measure housing and an inner surface of the tape hook. In one embodiment, a ratio of the upper hook height to the recess width is between 4:1 and 8:1. More specifically the ratio is between 4.5:1 and 7:1, even more specifically the ratio is between 5:1 and 6:1, and even more specifically the ratio of the upper blade height to the recess width is 5.5:1.

In one embodiment, the hook comprises a protrusion and a recessed portion that collectively define an inner surface. The protrusion extends closer to the tape measure housing than the recessed portion.

Another embodiment of the invention relates to a tape measure including a housing comprising a tape opening and a bumper extending below the tape opening. The bumper includes a recess surface located at least partially above the tape opening and a shoulder portion having an exterior surface. The recess surface is setback from the exterior surface of the shoulder portion defining a gap distance. The tape measure includes a reel rotatably mounted within the housing and an elongate blade wound around the reel. The elongate blade has an inner end coupled to the reel and an outer end extending out of the tape opening. The tape measure includes a hook assembly coupled to the outer end of the elongate blade. The tape measure includes a retraction system coupled to the reel, and the retraction system drives rewinding of the elongate blade on to the reel.

Another embodiment of the invention relates to a tape measure include a housing, a tape opening defined in the housing and a bumper coupled to the housing. The bumper includes a recess surface located at least partially above the tape opening, and an impact corner located below the tape opening. The impact corner is located in front of the recess surface defining a gap distance measured in the horizontal direction between the impact corner and the recess surface. The tape measure includes a reel rotatably mounted within the housing and an elongate blade wound around the reel. The elongate blade has an inner end coupled to the reel and an outer end extending out of the tape opening. The tape measure includes a hook assembly coupled to the outer end of the elongate blade and a retraction system coupled to the reel. The retraction system drives rewinding of the elongate blade on to the reel.

Another embodiment of the invention relates to tape measure including a housing, a tape opening defined in the housing and an impact protective corner extending below the tape opening. The tape measure includes a reel rotatably mounted within the housing and an elongate blade wound around the reel. The elongate blade has an inner end coupled to the reel and an outer end extending out of the tape opening. The tape measure includes a hook assembly coupled to the outer end of the elongate blade. The hook assembly includes an upper hook extending above the elongate blade and a lower hook extending below the elongate blade. A rear surface of the upper hook is setback from a rear surface of the lower hook defining a hook recess distance. The tape measure includes a retraction system coupled to the reel, and the retraction system drives rewinding of the elongate blade on to the reel.

Additional features and advantages will be set forth in the detailed description which follows, and, in part, will be readily apparent to those skilled in the art from the description or recognized by practicing the embodiments as described in the written description and claims hereof, as well as the appended drawings. It is to be understood that both the foregoing general description and the following detailed description are exemplary.

The accompanying drawings are included to provide further understanding and are incorporated in and constitute a part of this specification. The drawings illustrate one or more embodiments and, together with the description, serve to explain principles and operation of the various embodiments.

DETAILED DESCRIPTION

Referring generally to the figures, various embodiments of a tape measure are shown. Various embodiments of the tape measure discussed herein include an innovative bumper design that protects the tape blade and hook assembly. In various tape measures, the hook extends beneath the housing allowing users to place the tape measure against a work object, engage the hook against an edge of the work object, and move the housing away from the hook to extend the tape from the housing and other similar.

However, Applicant has determined that the overhang of the hook (i.e., the portion of the tape hook that extends beneath the lowest point of the housing or bumper) exposes the hook and tape blade to possible damage. For example, when the tape measure is subject to an impact (e.g., after being dropped), the hook and tape blade may receive at least part of the impact force when the hook's lower half impacts the ground first. This force can be transferred to the rivets (or other coupling structure) that couple the hook to the tape blade and to the tape blade itself.

Accordingly, in various designs discussed herein, Applicant has developed a tape measure, tape measure housing and/or bumper design that limits exposure of the tape blade and hook to such forces. In various embodiments discussed herein, the tape measure housing includes bumper with a shoulder that facilitates repositioning of the tape blade and hook during impact in a way that impact force is absorbed by the housing rather than by the hook or the tape blade. In general, the tape measure housing includes a bumper sized and shaped relative to the tape measure hook and/or tape opening to allow the tape hook to move upward and to pivot in a manner that decreases the impact force experienced by the tape hook and/or blade during impact.

As will be explained in detail below, in various embodiments, the shoulder of the bumper is coupled to the housing, and the tape blade transits an opening at least partially in the shoulder. At the moment of impact when the bottom surface of the tape hook initiates contact with a striking surface, the hook slides upward away from the ground until the bottom (lowermost edge or surface) of the hook is sub-flush with respect to the bottom of the bumper, allowing the bumper to contact the ground and to absorb the impact of the fall. In addition, the bumper described herein reduces forces exerted on the hook by providing a recess that allows the hook to move or to pivot inward during an impact on the ground, thereby further eliminating force that the hook experiences during impact.

Figure 1:
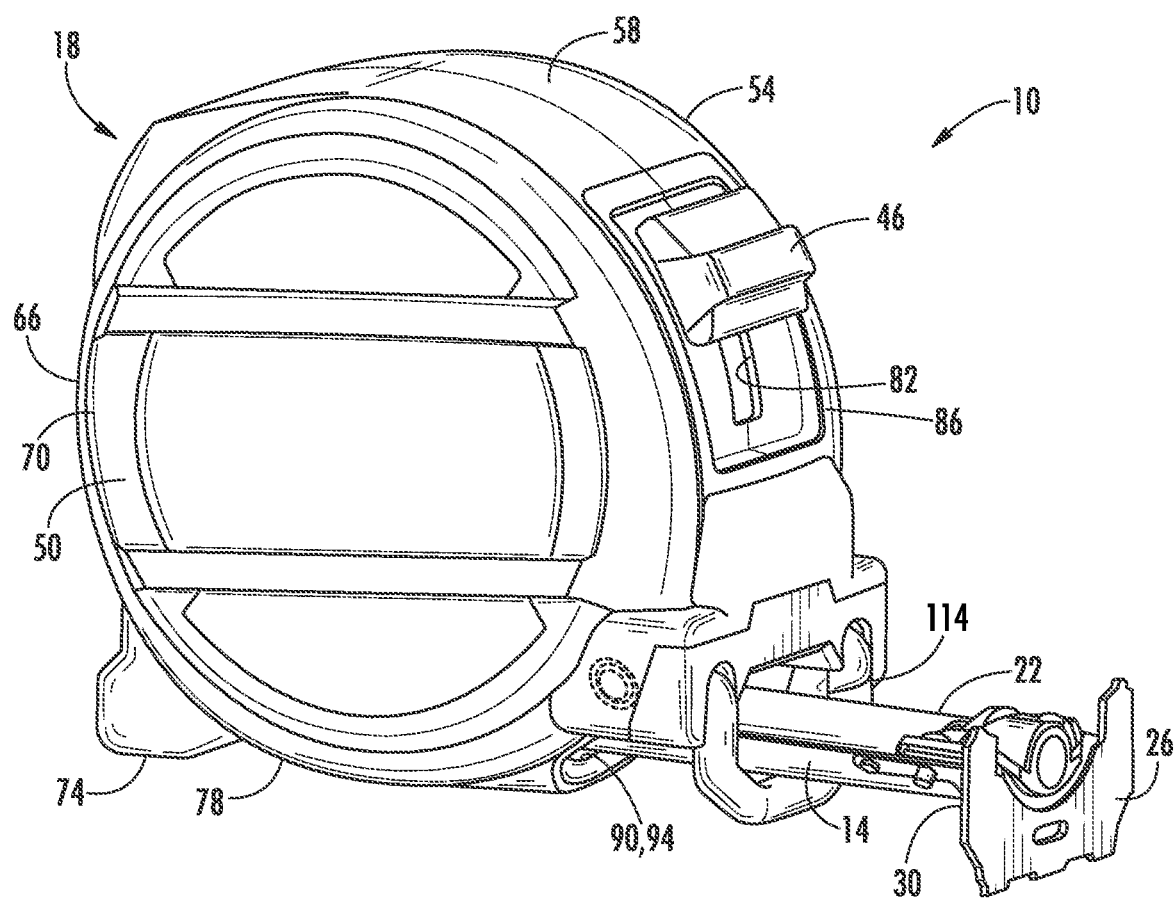
FIG. 1 is a left side perspective view of a tape measure, according to an exemplary embodiment.
Figure 2:
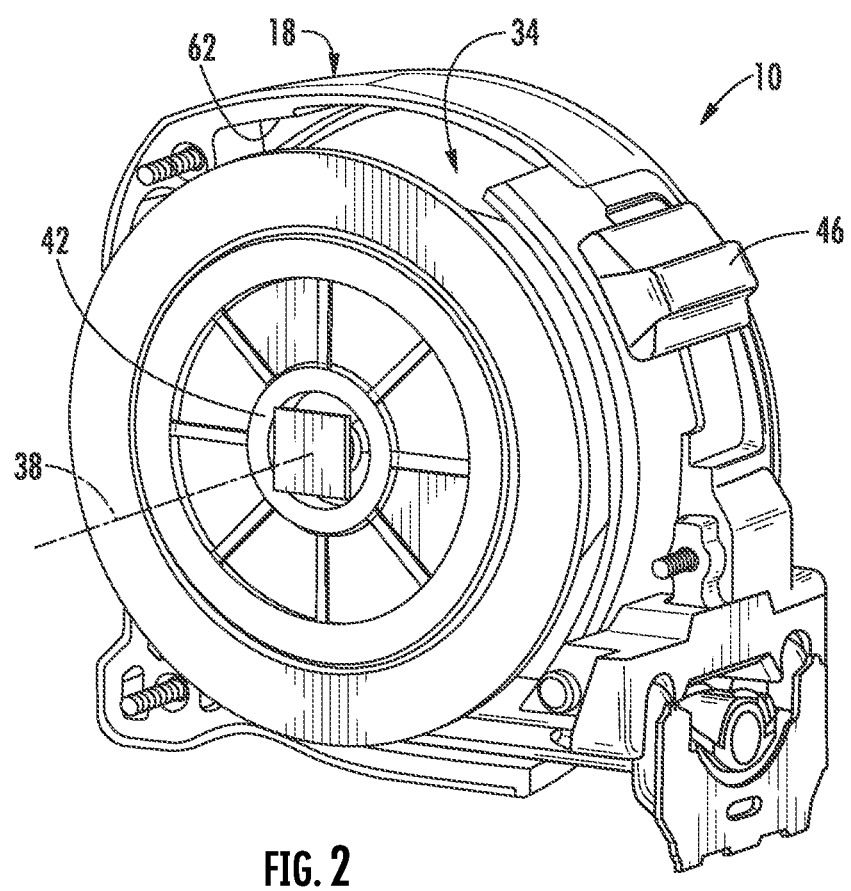
FIG. 2 is a left side perspective view of the tape measure of FIG. 1 with a portion of the tape measure housing removed, according to an exemplary embodiment.

Referring to FIG. 1 and FIG. 2, a tool, such as tape measure 10, is shown according to an exemplary embodiment. Tape measure 10 includes an elongate blade, shown as coilable tape blade 14, and a housing 18. In general, tape blade 14 is an elongate strip of material including a plurality of graduated measurement markings, and in specific embodiments, tape blade 14 is an elongate strip of metal material (e.g., steel material) that includes an outermost end coupled to a hook assembly, shown as hook assembly 26. Tape blade 14 may include various coatings (e.g., polymer coating layers) to help protect tape blade 14 and/or the graduated markings of the blade from wear, breakage, etc.

As shown in FIG. 1, a variable-length extended segment 22 of the tape blade 14 is retractable and extendable from the housing 18. Hook assembly 26 is fixedly coupled to an outer end portion 30 of tape blade 14. In various embodiments, tape blade 18 has a maximum length that may be extended from the housing of between 10 ft. and 50 ft.

As shown in FIG. 2, the non-extended portion of tape blade 14 is wound onto a reel 34, which is surrounded by housing 18. Reel 34 is rotatably disposed about an axis 38 of tape measure 10, and a retraction mechanism 42 is coupled to reel 34 and configured to drive reel 34 about rotation axis 38, which in turn provides powered retraction of tape blade 14. Retraction mechanism 42 may include one or more elongated spiral springs that provide the retraction energy to retraction mechanism 42. In other embodiments, retraction mechanism 42 includes other mechanisms such as one or more electric motors. A tape lock 46 is provided to selectively engage tape blade 14, which acts to restrain retraction mechanism 42 such that extended segment 22 of tape blade 14 remains at a desired length.

Referring to FIG. 1, housing 18 includes a first sidewall 50, a second sidewall 54, and a peripheral wall 58 connecting first sidewall 50 and second sidewall 54. First sidewall 50, second sidewall 54, and peripheral wall 58 define an internal cavity 62, shown in FIG. 2, in which reel 34 and retraction mechanism 42 are housed. Referring to FIG. 1, first sidewall 50 and second sidewall 54 have a substantially circular profile 66. In other embodiments, the sidewalls may be rectangular, polygonal, or any other desired shape. Portions of the housing 18 may be co-molded or separately formed of a resilient material, such as a natural or synthetic rubber. In the illustrated construction, housing 18 is formed with housing edge bumpers 70 and a support leg 74, which extends from a lower portion 78 of the peripheral wall 58.

A slot 82 is defined along a forward portion 86 of peripheral wall 58. Slot 82 provides an opening in the tape measure housing, which allows tape lock 46 to extend into housing 18. In addition, slot 82 provides a length sufficient to allow tape lock 46 to be moved relative to housing 18 between locked and unlocked positions.

Below the slot 82, a tape blade opening in the housing, shown as tape port 90, is provided in peripheral wall 58. Tape port 90 has an arcuate shape 94, corresponding to an arcuate cross-sectional profile of tape blade 14. The tape port 90 allows for the retraction and extension of tape blade 14 to and from the internal cavity 62 defined within housing 18.

Referring to FIGS. 3-8, details of innovative tape measure bumper designs that may be utilized with a tape measure, such as tape measure 10, discussed above, are shown. Thus, in such tape measure designs, tape measure 10 includes the innovative bumper design positioned in the front right corner (in the orientation of FIGS. 1 and 2) and generally in the region of the housing around tape opening 114. It should be understood that FIGS. 1 and 2 detail various components of tape measure 10, and details of a bumper design that may be utilized with tape measure 10 are shown in FIGS. 3-8.

Figure 3:
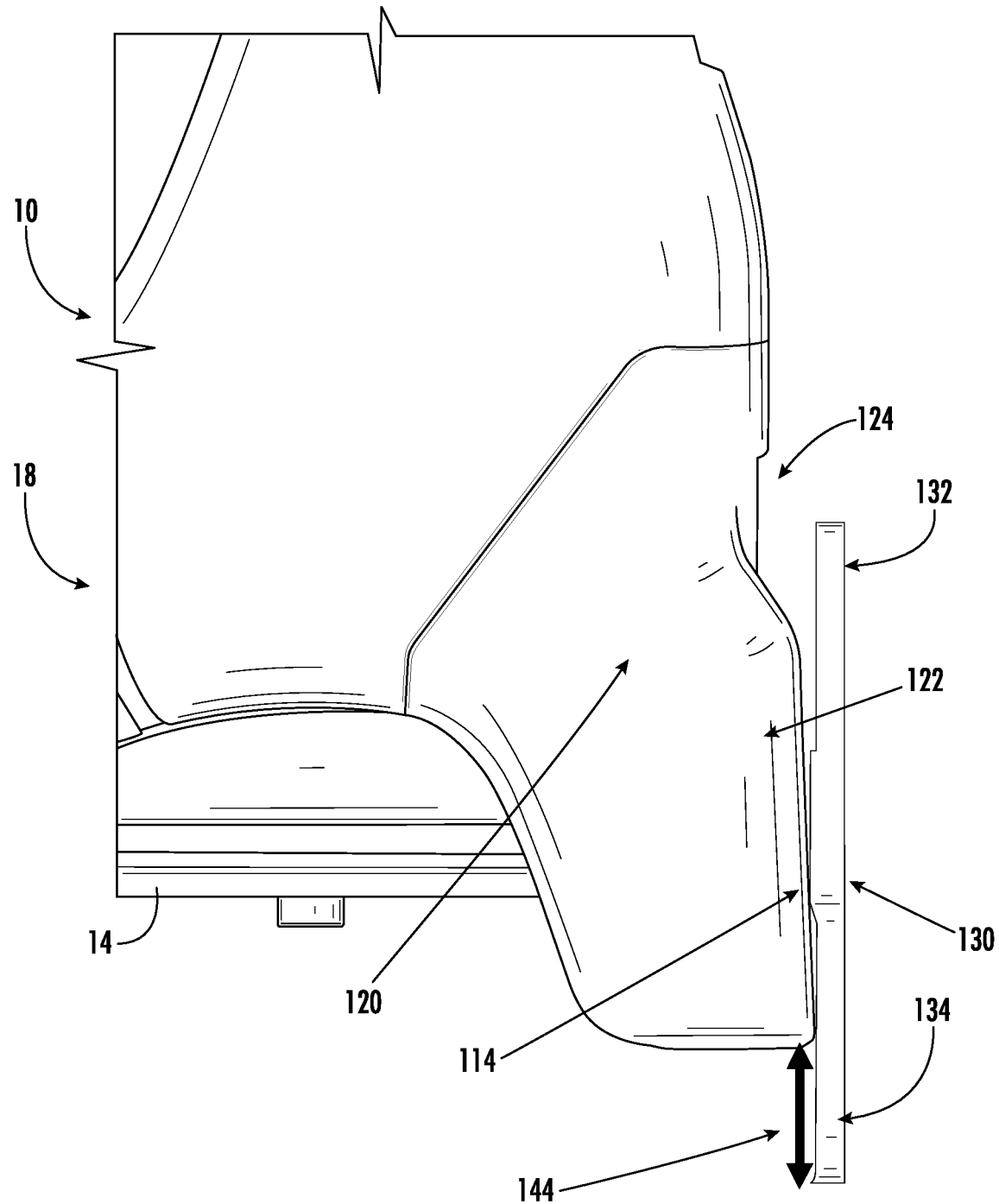
FIG. 3 is a side view of a tape measure bumper, according to an exemplary embodiment.
Figure 4:
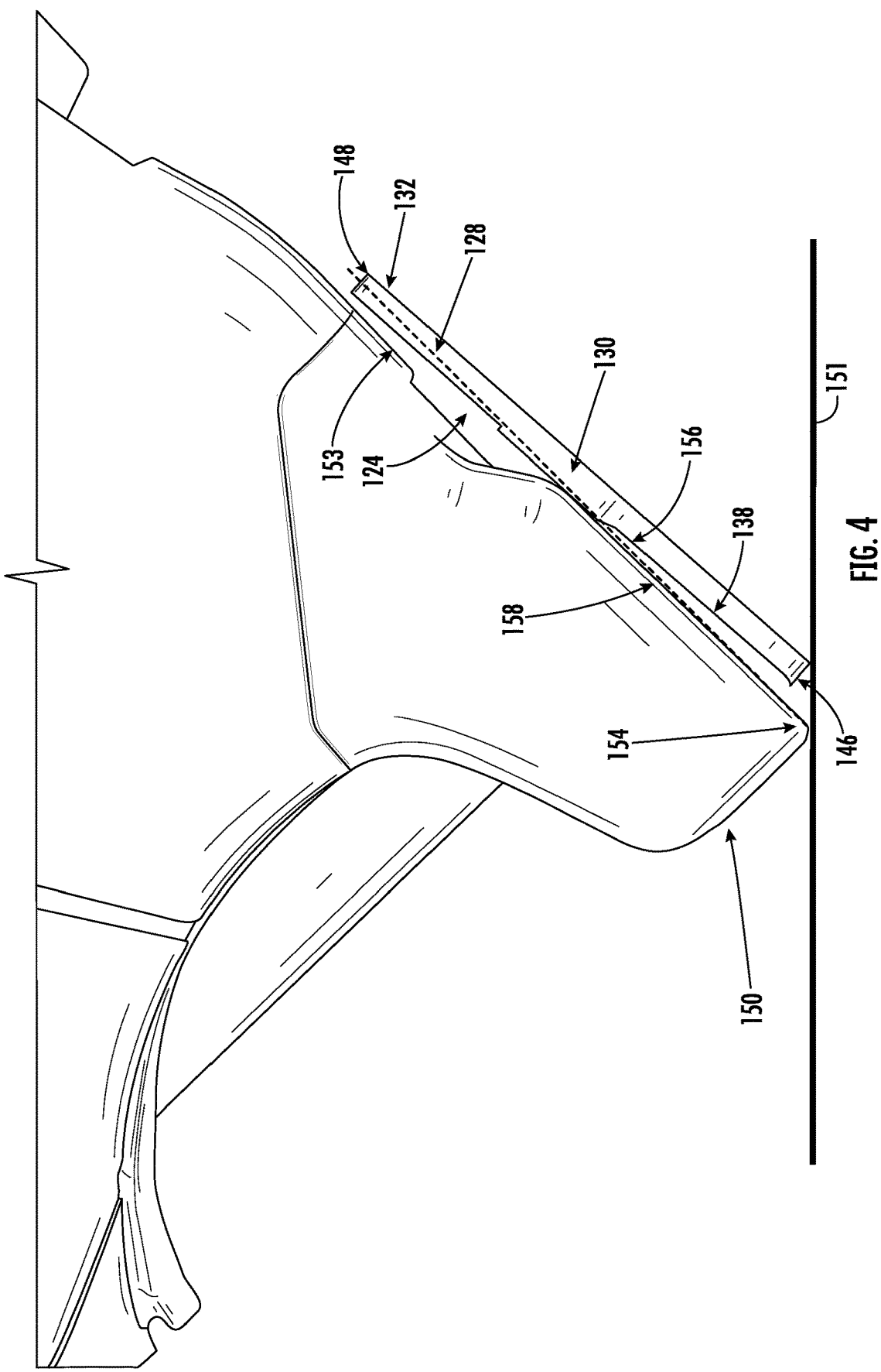
FIG. 4 is a detailed side view of the tape measure bumper of FIG. 3 shown during contact with a surface, according to an exemplary embodiment.
Figure 5:
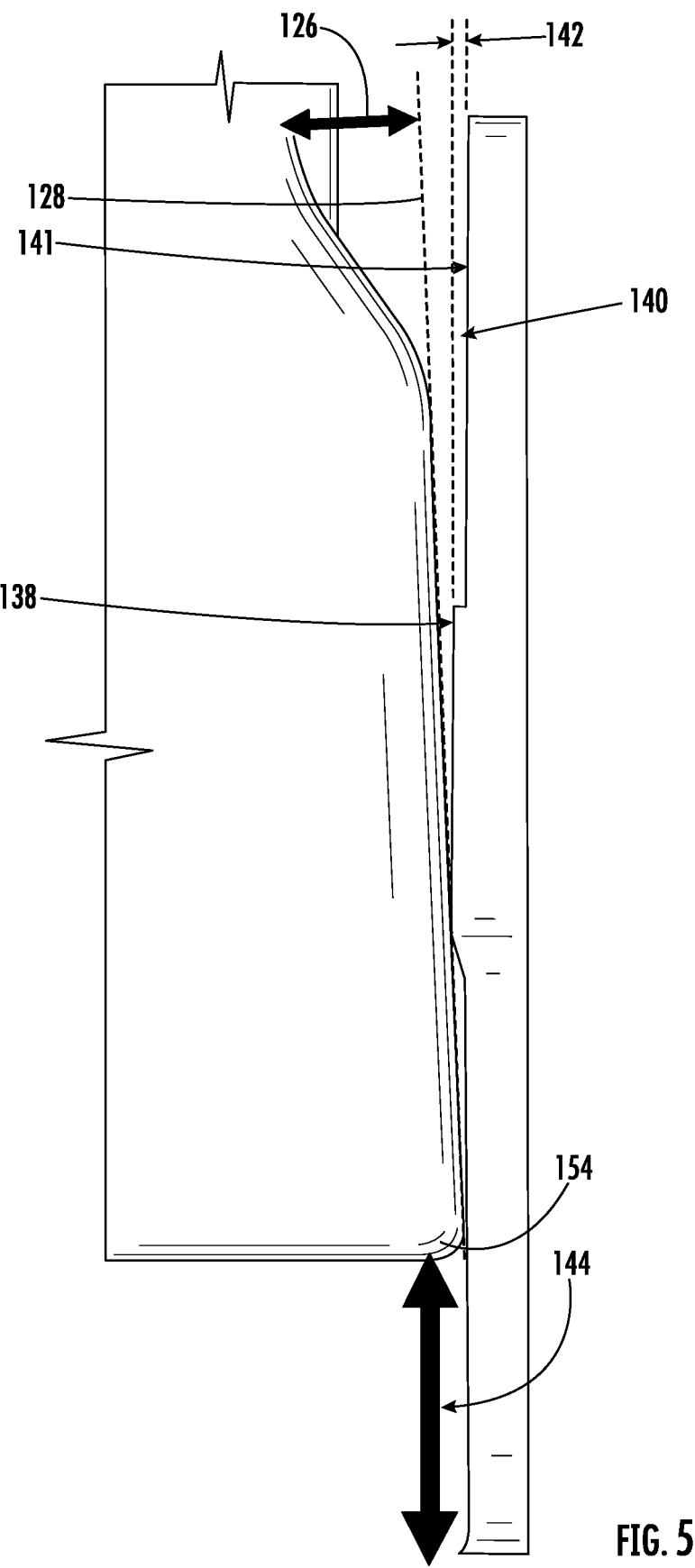
FIG. 5 is a detailed side view of the tape measure bumper of FIG. 3, according to an exemplary embodiment.

Referring to FIGS. 3-5, tape measure 10 includes housing 18 and a bumper coupled to housing 18, shown as bumper 120. As noted above regarding FIGS. 1 and 2, tape measure 10 includes a tape reel rotatably coupled to housing 18, an elongate tape blade wound around the tape reel, and a spiral spring coupled to the tape reel. One end of the tape blade is coupled to the tape reel, and the other end is coupled to hook 130.

In general, bumper 120 is a portion of tape measure housing that is located at the lower corner of tape measure housing 18 adjacent the tape opening 114. As shown in FIG. 3, bumper 120 includes shoulder 122, recess 124 and an impact protective corner, shown as corner 154. At least a portion of housing 18 that defines recess 124 also defines opening 114 through which the tape blade extends. In general, shoulder 122 is a portion of tape housing 18 that defines the forward most and lower most portion of tape housing 18, and the front surface of shoulder 122 defines a plane 128 (shown in FIG. 4). Recess 124 is defined by a portion of tape housing 18 that is set back from the front surface of shoulder 122 and that is above both tape opening 114 and shoulder 122. As will be discussed in more detail below, recess 124 provides a gap or space to allow movement of tape hook 130 during impact (instead of a rigid surface as would be the case in a tape housing with a flat front surface) which in turn limits the impact force imparted to tape hook 130 during impact with a surface such as the ground.

Hook 130 comprises upper hook 132, which extends above tape blade 14, and lower hook 134, which extends below tape blade 14. Lower surface 146 of lower hook 134 and upper surface 148 of upper hook 132 each face away from each other. For example when tape measure 10 is held by a user, lower surface 146 of lower hook 134 extends past lower surface 150 and corner 154 of bumper 120 by distance 144. In various embodiments, distance 144 is at least 3-4 mm, and more specifically distance 144 is 3-4 mm.

FIG. 4 illustrates the function of bumper 120 during impact with a striking surface 151, such as the ground. As shown in FIG. 4, at the moment of impact between tape measure 10 and striking surface 151, hook 130 and tape blade 14 moves upward relative to tape housing 18. As shown in FIG. 4, hook 130 moves upward until corner 154 of bumper 120 contacts striking surface 151. As hook 130 slides upward, hook 130 rotates slightly toward the front face of housing 18 (e.g., in the counter-clockwise direction in the orientation of FIG. 4), through plane 128 defined by the front face of shoulder 122. By allowing for more of the impact to be absorbed by bumper 120 before tape hook 130 encounters a portion of tape housing 18, the force experienced by tape hook 130 and tape blade 14 during impact is reduced, which Applicant believes will decrease the likelihood of damage to the tape hook or tape blade.

As shown in FIG. 4, this rotation of hook 130 also brings the upper portion 132 of hook 130 inward towards recess 124, thereby creating angle 156 between inner surface 138 of lower hook 134 and an outer or hook-interfacing surface 158 of shoulder 122. In various embodiments, angle 156 is at least 0.5 degrees, specifically is between 0.5 degrees and 20 degrees, and more specifically 2 degrees and 10 degrees. In contrast to a tape housing without recess 124, the bumper design discussed herein allows hook 130 to pivot a substantial distance, represented by angle 156, before contacting a portion of the tape housing above tape opening 114.

As shown in FIG. 5, recess 124 defines a gap distance. Gap distance 126 of recess 124 is the distance that outer surface 153 is set back from the front-most surface, e.g., surface 158, of bumper 120. In one embodiment, gap distance 126 can be defined as the horizontal setback distance between surface 153 and the front most surface at impact corner 154. Thus, gap distance 126 of recess 124 defines a distance over which upper hook 132 rotates before it interfaces the outer surface 153 of tape housing 18, which defines recess 124.

Referring to FIG. 5, to further increase the distance over which upper hook 132 is permitted to move or rotate prior to encountering a portion of tape housing 18, hook 130 is shaped to effectively increase the distance between the inner most surface 141 of upper hook 132 and outer surface 153. Thus, this shape defines a recess 140 along the inner surface of upper hook 132 that defining a hook recess distance 142, which is the orthogonal distance measured between inner surface 138 of lower hook 134 and surface 141 of upper hook 132. Gap distance 126 and recess distance 142 combine to provide a larger open space between surfaces 141 and 153 which in turn provides a larger rotational range over which upper hook 132 is allowed to rotate towards bumper 120 before upper hook 132 interfaces with recess 124 and/or housing 18. In a specific embodiment, gap distance 126 is 0.2 mm to 5 mm and specifically is 0.5 mm to 4.2 mm.

Figure 6:
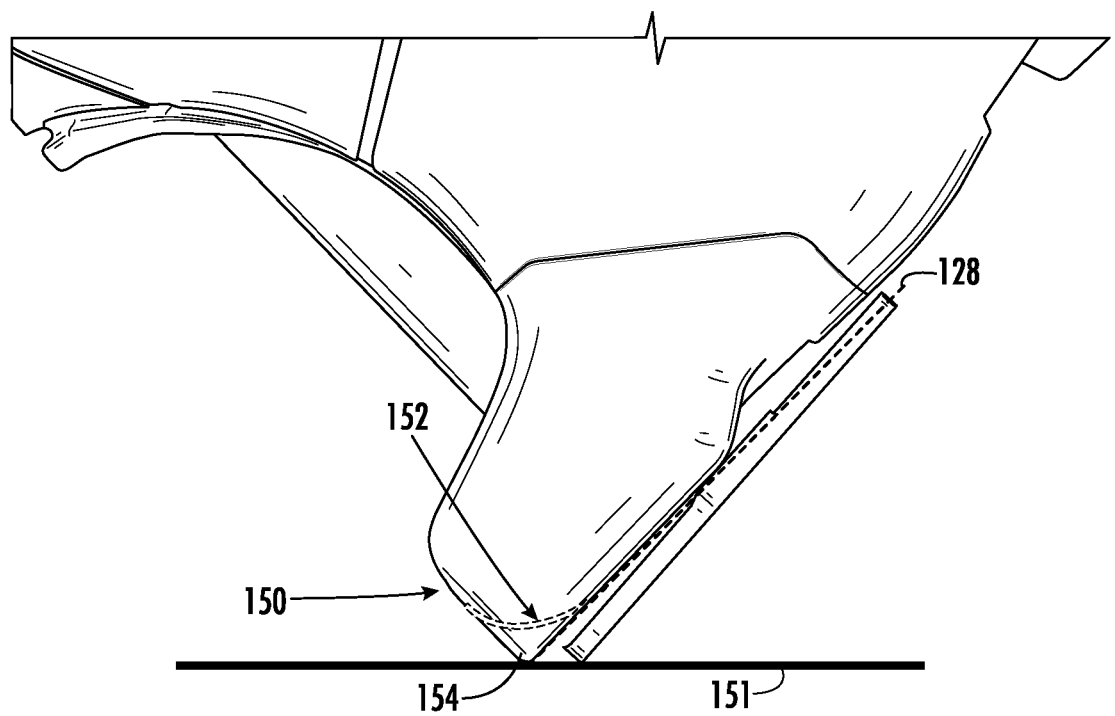
FIG. 6 is a detailed side view of the tape measure bumper of FIG. 3 shown during contact with a surface illustrating the function of the geometry of the bumper compared to a more rounded bumper geometry, according to an exemplary embodiment.
Figure 7:
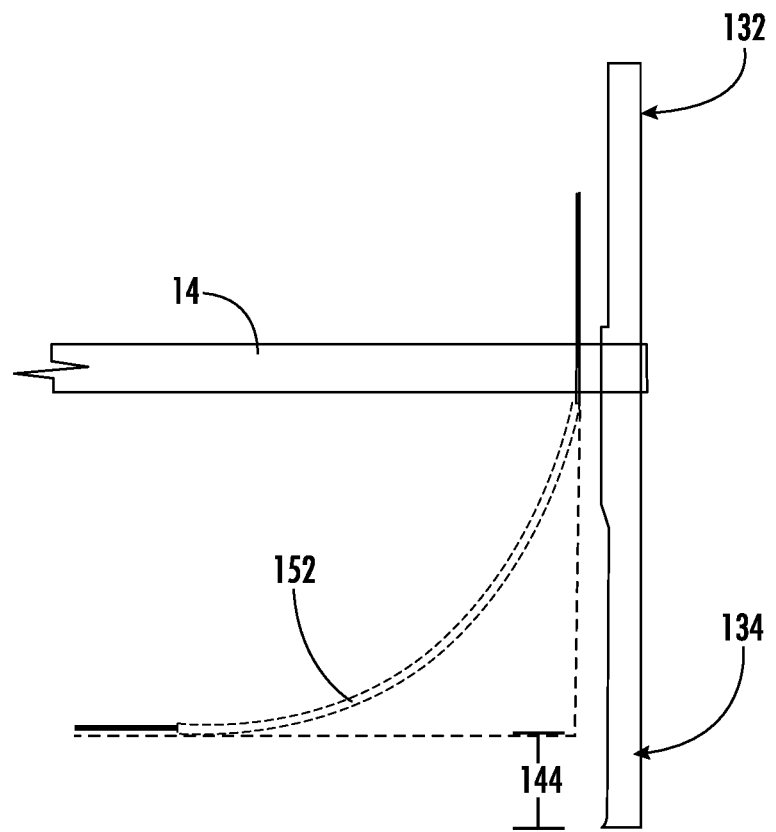
FIG. 7 is a schematic view of the tape measure bumper of FIG. 3 illustrating the relative size of a tape hook to bumper, according to an exemplary embodiment.

Referring to FIGS. 6-7, additional details of the interaction of bumper 120 with tape hook 130 during impact are shown. As compared to typical tape measure housing designs, impact protective corner 154 is shaped to have a shaper point (e.g., a smaller radius) than the typical tape measure housing corner, which improves impact performance. In various embodiments, the radius of curvature of corner 154 is between 0 mm and 2.5 mm, and specifically from 0.1 mm to 2.0 mm.

In general, during impact, corner 154 interfaces against striking surface 151 after hook 130 moves vertically away from the striking surface. By comparison, a bumper having a corner with a larger radius (e.g., more rounded) and/or a greater recess, shown as line 152, would require hook 130 to move vertically even further before the more rounded corner would interface against the striking surface. Thus, in such a design, either the tape blade opening would need to be larger in the vertical direction to provide for increased vertical tape movement or the impact would be absorbed by the tape hook prior to engagement of the bumper corner with the striking surface. This differential is illustrated schematically in FIG. 7.

However, Applicant has determined that simply increasing the height of the tape opening to accommodate large amounts of vertical tape movement during impact can result in other unsatisfactory tape performance issues. For example, Applicant has found that if the tape blade opening is too large in the vertical direction, tape standout distance can decrease and the degree of tape whip during retraction can increase. Thus, in the present design applicant has determined the size and shape of bumper 120 in combination with the vertical size of the tape opening provides a tape measure with both the drop performance provided by bumper 120 and standout and whip performance provided at least in part by a relatively small vertical height of the tape opening.

Figure 8:
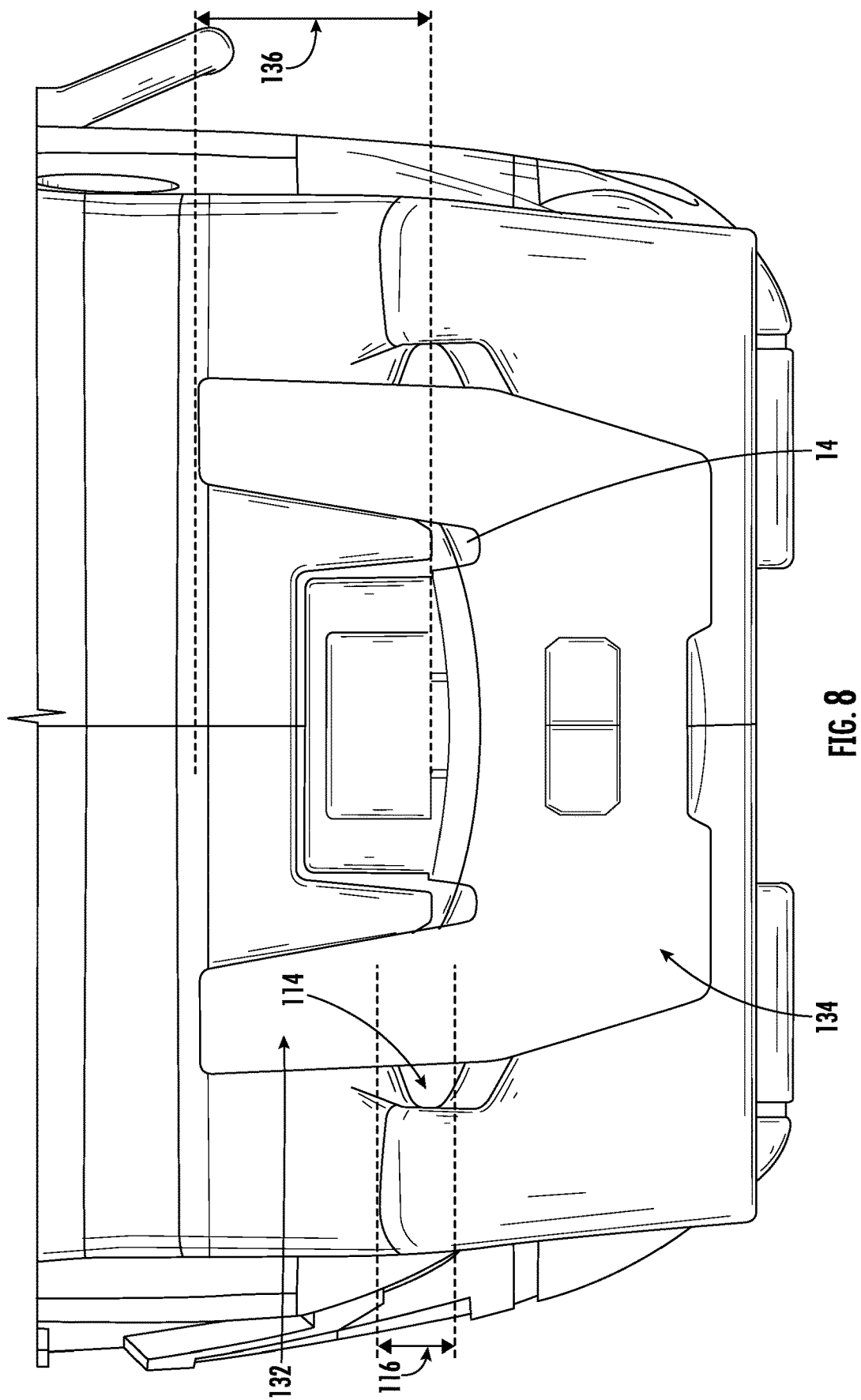
FIG. 8 is a detailed front view of the tape measure bumper of FIG. 3, according to an exemplary embodiment.

Referring to FIG. 8, upper hook 132 extends distance 136 above tape blade 14. As defined herein, distance 136 is measured from the top of the tape blade 14 to the top (e.g., the uppermost surface) of the wings of upper hook 132. As can be seen with reference to FIG. 4, the larger the distance 136 is, the more gap distance 126 (of bumper 120) and/or recess distance 142 (of hook 130) that is needed to accommodate rotation of tape hook 130 before upper hook 132 interfaces against surface 153 that defines recess 124.

Another factor that Applicant believes relates to the interaction of hook 130 with tape housing 18 during impact is height 116 of opening 114. As tape opening height 116 increases, the distance that upper hook 132 moves upward also increases. Thus, by utilizing a tape bumper design discussed herein, opening height 116 maybe relatively small while still providing for tape hook and blade protection because additional tape blade movement during impact is provided via rotation into recess 124 rather than relying on upward movement alone.

In various embodiments, Applicant has determined that the ratio of the upper blade height 136 to the gap distance 126 relates to the impact performance discussed herein. In one embodiment, the ratio of the upper blade height to the gap distance is greater than 3:1. In a specific embodiment, the ratio of the upper blade height to the gap distance is between 4:1 and 8:1. More specifically the ratio is between 4.5:1 and 7:1, even more specifically the ratio is between 5:1 and 6:1, and even more specifically the ratio of the upper blade height to the gap distance is 5.5:1.

In another embodiment, Applicant has determined that the ratio of the upper blade height 136 to the total gap distance (e.g., gap distance 126 plus distance 142) relates to the impact performance discussed herein. In one embodiment, the ratio of the upper blade height to the total gap distance is greater than 3:1. In a specific embodiment, the ratio of the upper blade height to the total gap distance is between 4:1 and 8:1. More specifically the ratio is between 4.5:1 and 7:1, even more specifically the ratio is between 5:1 and 6:1, and even more specifically the ratio of the upper blade height to the total gap distance is 5.5:1.

In one embodiment, opening 114 is defined entirely by shoulder 122. In an alternate embodiment, opening 114 is partially defined by bumper 120 and partially defined by housing 18, and housing 18 at least partially defines recess 124 into which hook 130 rotates.

In one embodiment, housing 18 and bumper 120 are separate components coupled together. In another embodiment, housing 18 and bumper 120 are molded as a single component. In various embodiments, bumper 120 is formed from a polymer material and may be formed from an impact absorbing polymer material.

Figure 9:
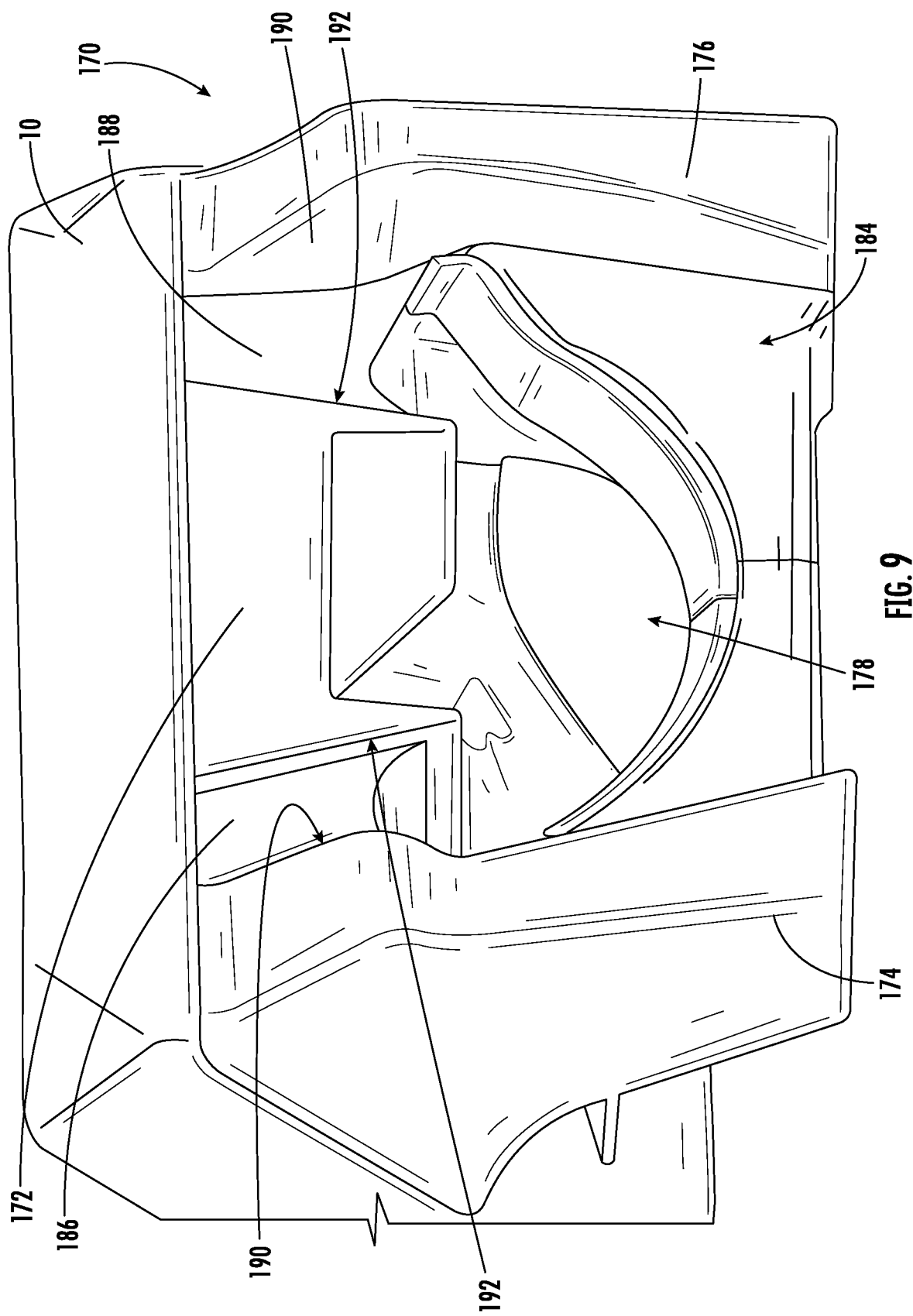
FIG. 9 is a perspective view of a tape measure bumper, according to an exemplary embodiment.
Figure 10:
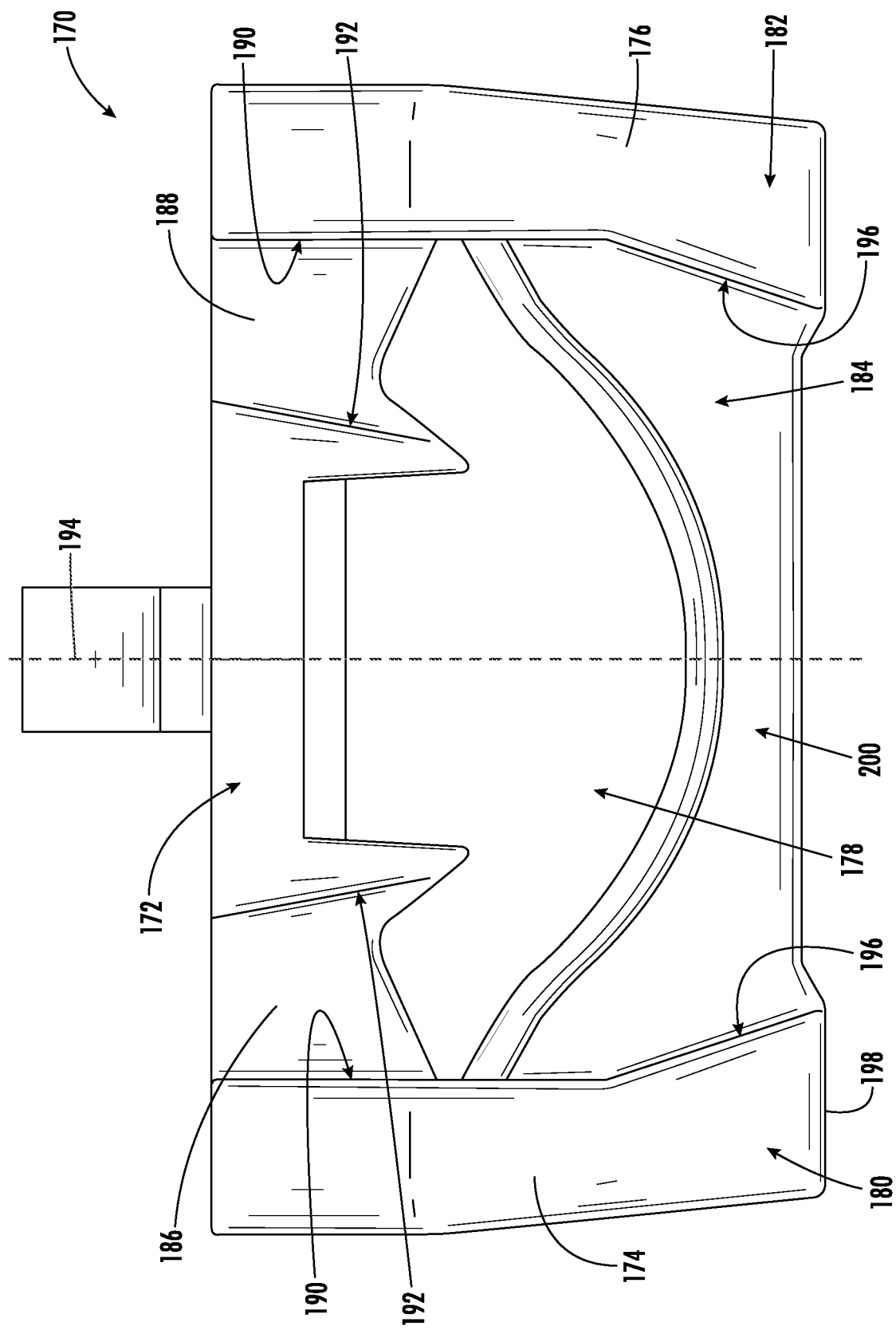
FIG. 10 is a front view of the tape measure bumper of FIG. 9, according to an exemplary embodiment.

Referring to FIGS. 9 and 10, a tape measure bumper 170 is shown according to an exemplary embodiment. Tape measure bumper 170 is substantially the same as bumper 120 discussed above, and tape measure bumper 170 may be utilized with tape measure 10, tape blade 14 and tape hook 130 as discussed herein. In general, tape measure bumper 170 includes a front face 172, a left sidewall 174, a right sidewall 176 and a tape opening 178 defined in front face 172. Left sidewall 174 and right sidewall 176 each include a front surface 180 and 182 that define the forward most surfaces of bumper 170.

Bumper 170 includes a central region 184 that recessed relative to surfaces 180 and 182 and surrounds tape opening 178. Specifically, central region 184 includes a first upper recess region 186 and second upper recess region 188. Upper recess regions 186 and 188 are located above left and right sides of tape opening 178. In general, recess regions 186 and 188 are shaped to receive upper hook portions 132 of tape hook 130 and provide extra space to receive and protect tape hook 130 during drop as discussed above.

Specifically, as shown best in FIG. 9, recess regions 186 and 188 are sloped rearward relative away from tape measure opening 178. In this arrangement a lower portion of each recess region 186 and 188 adjacent tape measure opening 178 is the forward most portion each recess portions 186 and 188. Recess portions 186 and 188 extend rearward in a direction towards the rear of the tape measure housing and away from opening 178. This sloped shape provides additional space for rearward pivoting of upper hook portions 132 during drop or other impact.

To further facilitate receipt of upper portions 132 of tape hook 130, each recess 186 and 188 are defined between outer sidewall 190 and inner sidewall 192. In general, the width dimension between sidewalls 190 and 192 is sized to closely accept upper hook portion 132 such that lateral movement of the tape hook is restricted via contact between sidewalls 190 and 192 during drop or other impact.

Similarly, to further provide a close fit to the upper portions 132 of tape hook 130, sidewalls 190 and 192 are positioned relative to each other to provide a shape similar to the shape of upper portions 132. Specifically, in the embodiment shown, sidewalls 190 are angled laterally inward toward central plane 194 of tape measure 10. Sidewalls 192 are angled laterally outward toward central plane 194 of tape measure 10.

Bumper 170 further includes lower, outer sidewalls 196. Lower, outer sidewalls 196 are contiguous with outer sidewall 190 and extend downward toward lower edge 198 of bumper 170. This arrangement defines a lower recess portion 200 located below tape opening 178 and defined laterally by lower outer sidewalls 196.

Lower recess portion 200 is recessed relative to surfaces 180 and 182, and is generally shaped to closely receive a lower portion 134 of tape hook 130. Similar to the arrangement of recesses 186 and 188, the closely conforming shape of lower recess portion 200 limits lateral movement of tape hook 130 during drop or impact further protecting tape hook 130. As shown, sidewalls 196 are angled inward toward plane 194 in a direction toward lower edge 198. In this arrangement, the lower end of recess portion 200 has a width that is less than the width of upper end of recess portion 200.

It should be understood that the figures illustrate the exemplary embodiments in detail, and it should be understood that the present application is not limited to the details or methodology set forth in the description or illustrated in the figures. It should also be understood that the terminology is for description purposes only and should not be regarded as limiting.

Further modifications and alternative embodiments of various aspects of the invention will be apparent to those skilled in the art in view of this description. Accordingly, this description is to be construed as illustrative only. The construction and arrangements, shown in the various exemplary embodiments, are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Some elements shown as integrally formed may be constructed of multiple parts or elements, the position of elements may be reversed or otherwise varied, and the nature or number of discrete elements or positions may be altered or varied. The order or sequence of any process, logical algorithm, or method steps may be varied or re-sequenced according to alternative embodiments. Other substitutions, modifications, changes and omissions may also be made in the design, operating conditions and arrangement of the various exemplary embodiments without departing from the scope of the present invention.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that any particular order be inferred. In addition, as used herein, the article "a" is intended to include one or more component or element, and is not intended to be construed as meaning only one. As used herein, "rigidly coupled" refers to two components being coupled in a manner such that the components move together in a fixed positional relationship when acted upon by a force.

Various embodiments of the invention relate to any combination of any of the features, and any such combination of features may be claimed in this or future applications. Any of the features, elements or components of any of the exemplary embodiments discussed above may be utilized alone or in combination with any of the features, elements or components of any of the other embodiments discussed above.

What is claimed is:

1. A tape measure comprising:
   a housing comprising a tape opening and a bumper extending below the tape opening, the bumper comprising:
      a recess surface located at least partially above the tape opening;
      a shoulder portion having an exterior surface;
      wherein the recess surface is setback from the exterior surface of the shoulder portion defining a gap distance;
   a reel rotatably mounted within the housing;
   an elongate blade wound around the reel, the elongate blade having an inner end coupled to the reel and an outer end extending out of the tape opening;
   a hook assembly coupled to the outer end of the elongate blade; and
   a retraction system coupled to the reel, wherein the retraction system drives rewinding of the elongate blade on to the reel;
   wherein the hook assembly includes a lower hook extending below the elongate blade and an upper hook extending above the elongate blade;
   wherein the upper hook defines a height extending above the elongate blade, wherein a ratio of the height of the upper hook to the gap distance is greater than 3 to 1.

2. The tape measure of claim 1, wherein the gap distance is between 0.2 mm to 5 mm.

3. The tape measure of claim 1, wherein a lowermost surface of the lower hook extends below a lowermost surface of the shoulder portion defining an overhang distance, wherein the overhang distance is at least 3 mm.

4. The tape measure of claim 1, wherein the upper hook is recessed relative to lower hook defining a hook recess.

5. The tape measure of claim 4, wherein the hook recess defines a hook recess distance that is less than the gap distance.

6. The tape measure of claim 1, wherein the shoulder portion defines an impact resistant corner having a radius of curvature is between 0 mm and 2.5 mm.

7. The tape measure of claim 1, where the retraction system includes a coil spring.

8. A tape measure comprising:
   a housing;
   a tape opening defined in the housing;
   a bumper coupled to the housing, the bumper comprising:
      a recess surface located at least partially above the tape opening;
      an impact corner located below the tape opening;
      wherein the impact corner is located in front of the recess surface defining a gap distance measured in the horizontal direction between the impact corner and the recess surface;
   a reel rotatably mounted within the housing;
   an elongate blade wound around the reel, the elongate blade having an inner end coupled to the reel and an outer end extending out of the tape opening;
   a hook assembly coupled to the outer end of the elongate blade; and
   a retraction system coupled to the reel, wherein the retraction system drives rewinding of the elongate blade on to the reel;
   wherein the gap distance is between 0.5 mm to 4.2 mm.

9. The tape measure of claim 8, wherein the hook assembly includes a lower hook extending below the elongate blade and an upper hook extending above the elongate blade.

10. The tape measure of claim 9, wherein a lowermost surface of the lower hook extends below the impact corner defining an overhang distance, wherein the overhang distance is at least 3 mm.

11. The tape measure of claim 10, wherein the upper hook defines a height extending above the elongate blade, wherein a ratio of the height of the upper hook to the gap distance is greater than 3 to 1.

12. The tape measure of claim 8, wherein the impact corner has a radius of curvature between 0.1 mm and 2.0 mm.

13. A tape measure comprising:
   a housing;
   a tape opening defined in the housing;
   an impact protective corner extending below the tape opening;
   a reel rotatably mounted within the housing;
   an elongate blade wound around the reel, the elongate blade having an inner end coupled to the reel and an outer end extending out of the tape opening;
   a hook assembly coupled to the outer end of the elongate blade, the hook assembly comprising:
      an upper hook extending above the elongate blade; and
      a lower hook extending below the elongate blade;
      wherein a rear surface of the upper hook is setback from a rear surface of the lower hook defining a hook recess distance; and
   a retraction system coupled to the reel, wherein the retraction system drives rewinding of the elongate blade on to the reel.

14. The tape measure of claim 13, the housing comprising a recess surface located at least partially above the tape opening, wherein a gap distance is measured in the horizontal direction between the impact protective corner and the recess surface.

15. The tape measure of claim 14, wherein the gap distance is greater than the hook recess distance.

16. The tape measure of claim 15, wherein the upper hook defines a hook height, wherein a ratio of the hook height to the sum of the hook recess distance and the gap distance is greater than 3 to 1.

17. The tape measure of claim 14, wherein the radius of curvature of the impact protective corner is between 0.1 mm and 2.0 mm.

18. A tape measure comprising:
a housing comprising a tape opening and a bumper extending below the tape opening, the bumper comprising:
  a recess surface located at least partially above the tape opening;
  a shoulder portion having an exterior surface;
  wherein the recess surface is setback from the exterior surface of the shoulder portion defining a gap distance;
a reel rotatably mounted within the housing;
an elongate blade wound around the reel, the elongate blade having an inner end coupled to the reel and an outer end extending out of the tape opening;
a hook assembly coupled to the outer end of the elongate blade; and
a retraction system coupled to the reel, wherein the retraction system drives rewinding of the elongate blade on to the reel;
wherein the shoulder portion defines an impact resistant corner having a radius of curvature is between 0 mm and 2.5 mm.

19. A tape measure comprising:
a housing;
a tape opening defined in the housing;
a bumper coupled to the housing, the bumper comprising:
  a recess surface located at least partially above the tape opening;
  an impact corner located below the tape opening;
  wherein the impact corner is located in front of the recess surface defining a gap distance measured in the horizontal direction between the impact corner and the recess surface;
a reel rotatably mounted within the housing;
an elongate blade wound around the reel, the elongate blade having an inner end coupled to the reel and an outer end extending out of the tape opening;
a hook assembly coupled to the outer end of the elongate blade; and
a retraction system coupled to the reel, wherein the retraction system drives rewinding of the elongate blade on to the reel;
wherein the hook assembly includes a lower hook extending below the elongate blade and an upper hook extending above the elongate blade;
wherein a lowermost surface of the lower hook extends below the impact corner defining an overhang distance, wherein the overhang distance is at least 3 mm.

20. A tape measure comprising:
a housing;
a tape opening defined in the housing;
a bumper coupled to the housing, the bumper comprising:
  a recess surface located at least partially above the tape opening;
  an impact corner located below the tape opening;
  wherein the impact corner is located in front of the recess surface defining a gap distance measured in the horizontal direction between the impact corner and the recess surface;
a reel rotatably mounted within the housing;
an elongate blade wound around the reel, the elongate blade having an inner end coupled to the reel and an outer end extending out of the tape opening;
a hook assembly coupled to the outer end of the elongate blade; and
a retraction system coupled to the reel, wherein the retraction system drives rewinding of the elongate blade on to the reel;
wherein the impact corner has a radius of curvature between 0.1 mm and 2.0 mm.

* * * * *